United States Patent
Barany

[11] Patent Number: 5,220,922
[45] Date of Patent: Jun. 22, 1993

[54] ULTRASONIC NON-CONTACT MOTION MONITORING SYSTEM

[76] Inventor: Laszlo P. Barany, 2181 Fayton Ct., Camarillo, Calif. 93010

[21] Appl. No.: 846,566

[22] Filed: Mar. 5, 1992

[51] Int. Cl.[5] .............................................. B61B 8/12
[52] U.S. Cl. ......................... 128/660.01; 128/661.07; 128/721; 367/94; 367/95
[58] Field of Search ........... 128/660.01, 660.02, 128/661.07, 661.04, 714, 721; 73/624; 367/95, 97, 93, 94

[56] References Cited

U.S. PATENT DOCUMENTS

| | | | |
|---|---|---|---|
| 3,803,539 | 4/1974 | MacMaster | 340/554 |
| 4,122,427 | 10/1978 | Karsh | 128/661.07 |
| 4,197,856 | 7/1980 | Northrop | 128/661.07 |
| 4,657,025 | 7/1987 | Orlando | 128/671 |
| 4,967,751 | 11/1990 | Sterzer | 128/721 |
| 5,086,775 | 2/1992 | Parker et al. | 128/661.07 |

FOREIGN PATENT DOCUMENTS 3885234 2/1974 Japan .

Primary Examiner—Kyle L. Howell
Assistant Examiner—George Manuel

[57] ABSTRACT

An ultrasonic non-contact motion monitoring system, useful for monitoring motional activities and such activities as respiration rate and heart beat rate. Using dual ultrasonic transducers, coherent sound waves are directed toward a moving subject. The phase frequency relationship of the reflected waves are compared to the transmitted sound waves in-phase and in phase-quadrature. The derived information, containing movement activity, is either displayed locally or sent to remote station(s) for display, processing and storage.

9 Claims, 2 Drawing Sheets

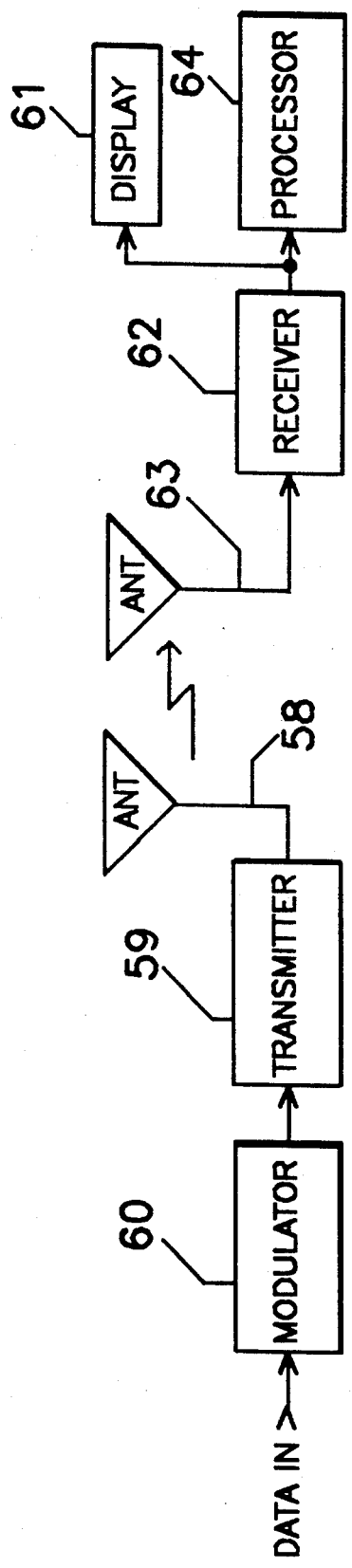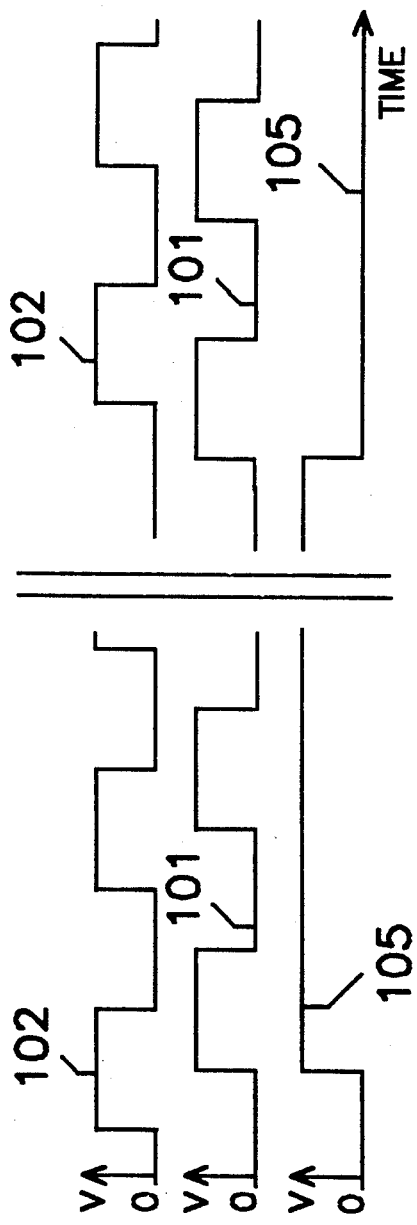

ULTRASONIC NON-CONTACT MOTION MONITORING SYSTEM

FIELD OF INVENTION

This application relates to monitoring motion and physiological activity such as respiration and heart beat of human beings and other living creatures, using ultrasonic means, without contacting the body with sensors in a form of belts, matches, electrodes and the like.

External movement of certain portions of the human body is indicative of physiological activity such as respiration and heart beat. These movements though being small in amplitude, are sufficient for monitoring and measuring the rate of respiration and heart beat without making contact to the body For automatic operation of some diagnostic equipment in certain clinical application, the direction of body motion must be indicated, even for involuntary subjects such as infants and the like. Some serious life threatening breathing and heart beat disorders can occur in human beings at any age which are difficult to detect unless a reliable means of continuous non-contact monitoring is available.

BACKGROUND OF INVENTION

The various issued patents in the ultrasonic and RF respiration monitor field have been the teaching of phase comparison means. Accordingly, some suitable probe is set to emit sufficient energy at a frequency on or about 40 kHz in the case of ultrasound and about 10 gHz in the case of RF, onto the chest cavity or other body portion of the subject. A similar probe to that which was used for transmission, receives some of the energy reflected back from the subject. Movement of the chest cavity and other body parts caused by respiration and heart beat effect the phase of the received energy relative to the phase of the transmitted energy. Since such movements change the length of the path over which the transmitted and received signal travel, the information of movement is contained in the phase. Finally, a suitable phase detector is used to recover the difference in phase which is indicative of movement.

This method of movement monitoring can be effective in certain application. However, the practical utilities of this phase comparison method have not been solved effectively. We can illustrate with the following expression describing the phenomenon $$\theta = 4\pi d/L \text{ radians} \tag{1}$$

Where
- L = wave length C/OF, in cm.
- C = velocity of the signal in the medium, in cm/sec
- FO = center frequency of the signal, in Hz From expression (1) it is evident that the phase angle $\theta$, is a strong function of the path length d. In particular, it is the round trip for the signal from the transmitter probe to the subject and back to the receiving probe. Distance d, and hence phase angle $\theta$, will change due to the rhythmic physiological movement such as respiration and heart beat, assuming the occurrence of no other physical movement of the subject. More specifically, assume that the total distance d, traveled by the signal from probe to subject and back is several wave lengths (which it will be in a practical application) and $\delta d$ is the incremental distance change in d, due to rhythmic physiological activity. Accordingly, if $d + \delta d$ exhibits a phase lag of any integral multiples of $2\pi$ radians or more, the phase detector output will exhibit a stationary phase component $\theta s$ due to d, and $\theta \delta$ due to $\delta d$. The phase detector output in this region, that is about 0 and $2\pi$ radians, will exhibit serious ambiguities due to the multivalued transfer characteristics of the device.

The seriousness of the problem can be appreciated when the total path length d, falls right on 0 or $2\pi$. In this situation a double output is given by the phase detector due to $\delta d$. Some systems employing this so called open-loop embodiment compromise the operation by having a caretaker physically make an adjustment in distance d, (i.e., move the apparatus slightly closer or further from the subject) in order to operate on the usable portion of the phase detector.

Other teachers of the art use phase lock means to alleviate $\delta \theta$ from the dependence of the initial value of d. In this embodiment the fixed frequency oscillator is replaced with a voltage controlled oscillator whose frequency is now adjusted by an integrator integrating the output of the phase detector. In this arrangement the loop is closed and, $\delta \theta$, due to $d + \delta d$, always approaches zero because of the integrator in the loop system.

While this phase locked means seems a workable solution the fact remains that such a system suffers, among others, most notably from the requirement of having a very low loop band-width. To illustrate this, it is known from clinical observation that in some situation the respiration rate of a person can be as low as 0.3 Hz. In order to track, and not track out, such a low frequency of motion the loop band-width should be at least about 0.03 Hz. For those who are well-versed in the electronic art know that such a low loop band-width over taxes component values in terms of inherent drift and leakage, resulting in overly touchy circuits, loop instability, slow start-up and frequent dangerous falling out of lock condition. In some application circuitry have been added to indicate loop out of lock, to speed up loop lock and to reduce drift. Invariably, these circuits are complex and, above all, they are also a control system with associated problems of their own. As a result, enhancements such as these can lead to further loop confusion and the over all effectiveness does not prove to be an advantage.

The ultrasonic non-contact motion monitor system of the present invention is distinct from the prior art in the following ways: Unlike the prior art, wherein the teaching is to illuminate the moving subject with waves whose wave lengths much longer then the physical dimensional extent of the movement the present invention teaches that the illuminating wave length must be much shorter then the smallest physical dimens extent of the moving subject. This teaching directs attention to requiring that the wave length of the operating ultrasonic wave be at least one half of the minimum extent of the movement being monitored. This implies that the operating frequency for this invention is to be much higher then previous systems for this application, resulting in dramatic improvement in system performance.

The attention is directed so as to obtain sufficient number of samples from the physical dimensional extent of the movement in order to characterize sufficiently the observed motion. As an example, an assumption can be made that the extent of a one way movement of a subject toward the system is 0.1 cm. In order to get at least two samples, the wave length of the ultrasonic wave should be less then 0.05 cm. Now if the speed of sound in air is close to 34359 cm/sec then the required frequency for the internal system oscillator should be about 687,180 Hz, calculated from the expression $FO=C/L$. This is nearly 20 times increase over the 40 kHz systems.

Another requirement of the present invention is that the phase of the returned signal from the moving subject is to be compared with the transmitted signal, in-phase, and in phase-quadrature (i.e., shifted by 90°). This is important for identifying movements toward or away from the apparatus. Since this method identifies the direction of motion, a means can be provided to count the chamber of times, in a given interval, change in direction occurred. From this data movement rate is determined.

Increasing the frequency of the monitoring apparatus yield the inherent advantage of narrower beam-width and higher gains from the transmit and receive transducers. Narrow beam-width allows the sonic energy to be focused to a desired spot on the subject thus avoiding the interference from nearby undesirable movements. Additionally, phase locking and the associated problems are avoided; in stead, the system operates on turn-on, requires no critical components and touchy tuning. Furthermore, the initial value of distance d is no longer of any consequence.

SUMMARY OF THE INVENTION

The preferred embodiment motion monitor of the present invention comprises of the following: a continuous wave oscillator for driving an acoustic radiator which exits the ultrasonic sound waves directed toward the subject under surveillance. The waves reflected back from the subject to a sound receiving transducer whose output is compared to the phase of the continuous wave-oscillator, in-phase I, and in phase-quadrature Q. Following the I & Q phase comparators the signals are appropriately band limited with bandpass filters. The outputs of the filters are passed to I & Q Schmitt triggers with hysteresis to enable digital processing. The output of the in-phase 1, logic level is connected to the data input of a "DATA" flipflop, and the quadrature a logic level is connected to the clock input of the same flipflop. The output of the flipflop is sent to a digital counter and other digital processing components for further processing.

BRIEF DESCRIPTION OF DRAWING

FIG. 2 is a schematic block diagram of a typical radio transmission system.

FIG. 3 is a schematic block diagram of a typical remote radio receiving system.

FIG. 4 is a waveform diagram showing in-phase channel signal 102 leading in quadrature-phase channel signal 101, resulting in the high logic level output signal 105.

FIG. 5 is a waveform diagram showing in-phase channel signal 102 lagging in quadrature-phase channel signal 101, resulting in the low logic level output signal 105.

DETAILED DESCRIPTION OF PREFERRED EMBODIMENT

Figure 1:
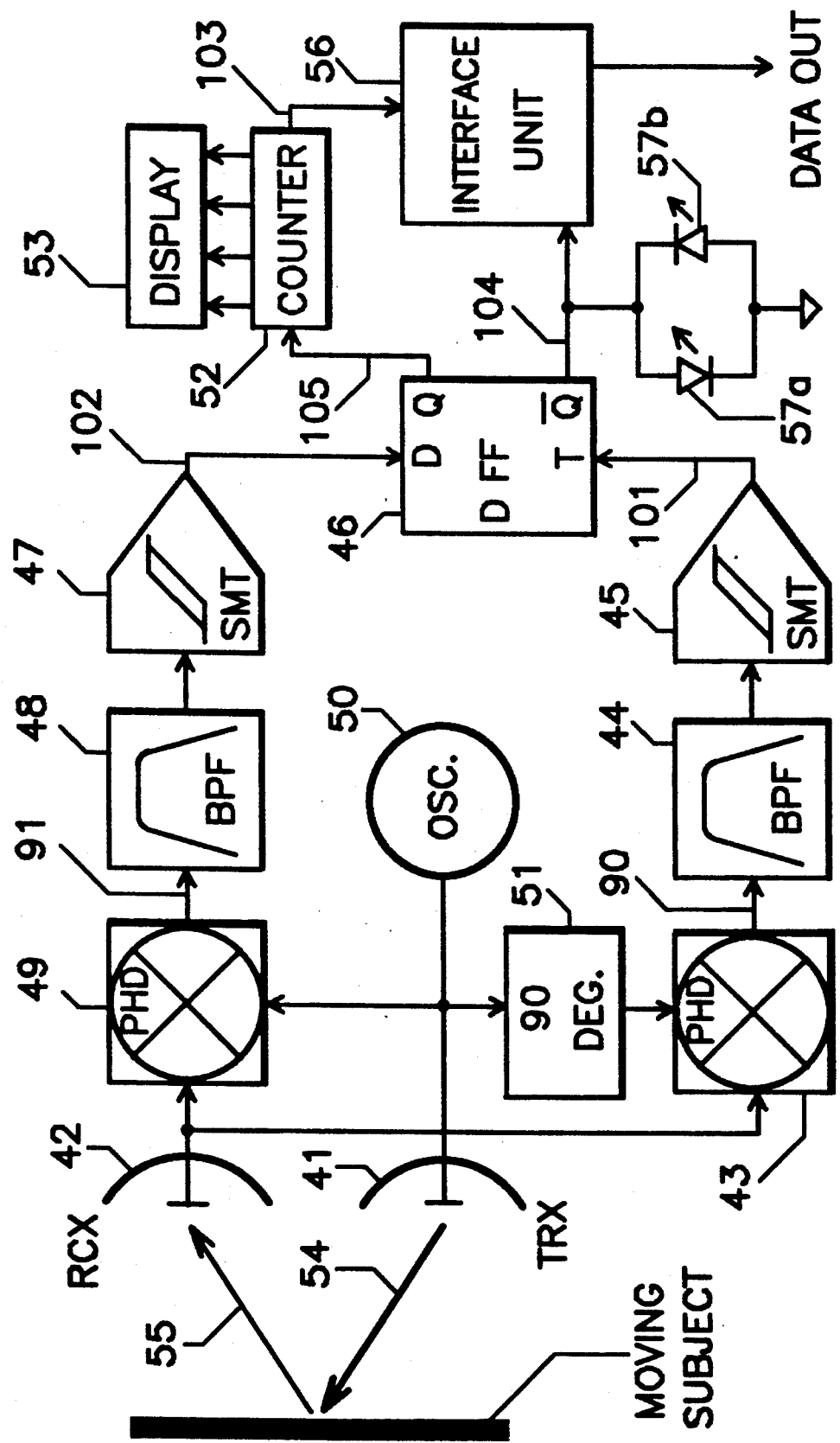
FIG. 1 is a schematic block diagram of the present dual transducer version of the invented system.

Referring to FIG. 1, an oscillator 50 producing a continuous sine wave is coupled to an appropriate ultrasonic transducer 41 sending ultrasonic sound waves 54 toward the subject under surveillance. Sound receiving transducer 42 responsive to reflected ultrasonic sound waves 55 from the moving subject, produces a sound wave responsive voltage signal at its output. Phase signal voltage comparator 49 compares transducer 42 signals with the voltage signal from oscillator 50, producing a preferred difference signal 91 at its output. Likewise, phase signal voltage comparator 43 compares transducer 42 signals with voltage signals, except shifted 90° by phase shifter 51 from oscillator 50, producing a preferred difference signal 90 at its output.

The difference signal 91 from either phase comparator 49 is are bandpass filtered by bandpass filter 48. The resultant signal represents the differences in phase measured between the sent and received signals within the frequency band of the filter. This signal, which represents motion of the subject, is connected to Schmitt trigger circuit 47, whose output is the digital signal 102.

In the like manner, the difference signal 90, 43 is are bandpass filtered by bandpass filter 44. The resultant signal represents the differences in phase measured between received and 90° shifted version of the sent signal within the frequency band of the filter. This signal, which represents motion of the subject, is connected to Schmitt trigger circuit 45, whose output is the digital signal 101.

Schmitt trigger 45 and 47 have a hysteresis level set to reject minor signal variances of no interest and to establish a system threshold level. They produce a digital logic output signal at their output which switched its state each time a zero crossing (±hyst. Voltage) occurs due to signals representing motion of the subject.

In FIG. 1, digital signal 101 is connected to the clock "T" input of flipflop 46. Also, digital signal 102 is connected to the "D" input of flipflop 46. The Q output signal 105 of flipflop 46, representing TO and FROM movement of the subject relative to the apparatus, is routed to counter 52 which is updated so as to provide movement rate, which is displayed by display 53. There is also a counter status digital signal 103 available for use by other devices. The Q-not output of flipflop 46 is also connected to a pair of light emitting diodes 57a and 57b in such a way as to have the cathode of one opposite to the other. In this manner, when they are appropriately labeled they indicate direction of motion.

Also in FIG. 1, a digital interface unit 56 is provided which receives digital signals 103 and 104 from counter 52, and flipflop 46, as well as analog signals from selected parts of the system. This unit converts the received information to serial and/or parallel digital data for transmission to remote stations.

FIG. 2 depict a form of data transmission means by electromagnetic waves. Modulator 60 is capable of interfacing to digital interface unit 56 and is directed to modulate a carrier electromagnetic wave with motion bearing digital and other information. Transmitter 59 power amplifies the combined signals and sends it antenna 58. Antenna 58 provides the impedance matching between transmitter device 59 and free space so that the modulated electromagnetic wave can reach a remote receiver.

The remote receiver in FIG. 3, consists of receiving antenna 63 which receives the electromagnetic waves sent by the transmitter unit. The antenna 63 is connected to receiver demodulator 62. The demodulated base-band digital information is displayed in display unit 61 or passed on to a digital computer 64, for storage or further processing.

Referring to FIG.1, the operation of the movement monitoring system will be described (for reference see for example, S.A. Hovanessian, "Radar System Design and Analysis," Artech House., and M. Skolnik, "Introduction to Radar Systems," McGraw-Hill, 1962, pp. 82-83). The ultrasonic signal produced by oscillator 50 is of a form $$Et = Eo \cos(\Omega o)t \quad (2)$$

The reflected signal from the moving subject will be $$Er = Eo \cos\{(\Omega o \pm \delta d)t + \theta\} \quad (3)$$

where
Eo = amplitude of transmitted signal
Ω = angular frequency of oscillator 50, radiane/sec
δd = Doppler angular frequency shift
θ = a constant stationary phase shift which depends on the total path length d, over which the ultrasonic wave travels.

The sign of the doppler frequency δd and θ will depend on the direction of the movement of the subject. This direction may be found by splitting the received signal into two channels as shown in FIG. 1. The received signal and the portion of the transmitted signal are compared in phase by detector 49 to yield a difference signal 91 which is the A channel. After filtering, the signal of interest is $$Ea = Eo \cos(\pm \omega dt + \theta) \quad (4)$$

The other similar, except for the 90° phase delay introduced in the signal of oscillator 50. The output of the phase detector channel B, signal 90, after filtering is $$Eb = Eo \cos(\pm \delta dt + \theta + \tfrac{1}{2}\pi) \quad (5)$$

If the monitored subject is moving toward the apparatus the output from the two channels are $$Ea(+) = Eo \cos(\Omega dt + \theta),\ Eb(+) = Eo \cos(\delta dt + \theta + \tfrac{1}{2}\pi) \quad (6a)$$

On the other hand, if the subject is moving away from the apparatus $$Ea(-) = Eo \cos(\Omega dt - \theta),\ Eb(-) = Eo \cos(\Omega dt - \Omega - \tfrac{1}{2}\pi) \quad (6b)$$

In order to determine if channel A leads or lags channel B, it is necessary to observe the relative phase between the two channels. This is accomplished by feeding channel A, signal 102, to the data (D) input of a D-flipflop 46, while feeding channel B, signal 101, to the clock (T) input of the D-flipflop. The output Q of 46, signal 105, will be at a logical high level as long as the movement of the subject is toward the system. As shown in FIG. 4, channel B, signal 101, will be lagging channel A, signal 102 by 90°, implying that a logical high is present at the D input of flipflop 46 before the clock T, signal 101, arrives. When, how ever, the subject is moving away from the apparatus, equation (6b), channel B, signal 101, is leading in phase, implying the absence of a logical high at the D input when the clock signal 101 arrives.

Referring to FIG. 5, it follows then, that clock signal 101 clocks a logical zero into flipflop 46, causing output Q to go to a low logic level, as shown by signal 105.

When the "TO" and "FROM" LED indicators 57a and 57b, along with counter 52 is attached to Q and Q-not outputs of flipflop 46, movement rate and direction of motion indication information are provided.

What is claimed is:

1. A non-contact ultrasonic motion monitoring system for monitoring physiological functions of a moving subject comprising:
   (a) a stable oscillator for generating a continuous signal and,
   (b) a means for selecting the frequency of said signal generated by said stable oscillator and,
   (c) a transmitting ultrasonic transducer to transmit said signal to illuminate said moving subject with sound wave and,
   (d) the frequency of said signal of said stable oscillator is set with thereon frequency selection means in order that the wave length of said transmitted sound waves is substantially at least ½ times shorter than the expected minimum dimensional extent displaced by said moving subject and,
   (e) a receiving ultrasonic transducer to receive the reflected sound waves indicative of physiological motion from said moving subject, thereby converting it into motion responsive signals and,
   (f) a means for splitting said motion responsive signals into a first received signal portion and into a second received signal portion and,
   (g) a means for multiplying said first received signal portion with said stable oscillator signal, substantially in phase, therein containing difference signals indicative of the phase difference between said transmitted and said reflected sound waves and,
   (h) a means for filtering said received signals corresponding to motion responsive signals of said moving subject and,
   (i) a comparator receiving said motion responsive signals whereby each time said motion responsive signals passes a set threshold with a positive slope and subsequently recrosses a slightly different threshold with a negative slope, thereby producing a digital output pulse signal and,
   (j) a D-flipflop having the data input thereof receiving said digital output pulse signal of said comparator and,
   (k) a means for multiplying said second signal portion with said stable oscillator signal, substantially in quadrature phase, therein containing difference signals indicative of the phase difference between said transmitted and said reflected sound waves and,
   (l) a means for filtering said received signals corresponding to a range of expected motion responsive signals of said moving subject and,
   (m) a comparator receiving said motion responsive signals whereby each time said motion responsive signals passes a set threshold with a positive slope and substantially recrosses a slightly different threshold with a negative slope, thereby producing a digital output pulse and,
   (n) said D-flipflop having the clock input thereof receiving said digital output pulse of the said comparator.

2. The system as defined in claim 1, wherein the Q-output of said D-flipflop flips to a logical high digital logic level as long as the movement of said moving subject under surveillance exhibits a continuous movement toward said ultrasonic transmit and said receive transducers and, wherein the said Q-output fo said D- flipflop flips to a logical low digital logic level as long as the movement of said moving subject under surveillance exhibits a continuous movement away from said ultrasonic transmit and said receive transducers.

3. The system as defined in claim 1, wherein the Q-not output of said D-flip flop is connected to a light emitting diode labeled TO to illuminate when ever said Q-not output is at a logical low digital logic level.

4. The system as defined in claim 1, wherein the Q-not output of said D-flip flop is connected to a light emitting diode labeled FROM to illuminate when ever said Q-not output is at a logical high digital logic level.

5. The system as defined in claim 1, wherein said Q-output of said D-flipflop provides clock pulses, being the result of rhythmic moving activity of said moving subject, to a binary digital counter with a display of count attached to it and, said counter being refreshed at certain time intervals to display the rate of rhythmic motion of said moving subject.

6. The system as defined in claim 1, wherein an interface unit is provided in order that any motion responsive information signal of interest produced by said ultrasonic non-contact motion monitoring system in response to a moving subject is converted by an analog/digital conversion means to provide a standard digital parallel and serial data port for the attachment of peripheral equipment.

7. The system as defined in claim 6, wherein a transmitting means is provided via current conducting cable, attached to said interface unit, wherein contained said motion responsive and said other electrical signals produced by said ultrasonic non-contact motion monitoring system in response to a moving subject are transmitted to a remote observer unit.

8. The system as defined n claim 6, wherein a transmitting means is provided via electromagnetic caves, attached to said interface unit, wherein contained said motion responsive and said other electrical signals produced by said ultrasonic non-contact motion monitoring system in response to a moving subject are transmitted to remote observer units.

9. The system as defined in claim 8, wherein contained said motion responsive signals and said other electrical signals produced by said non-contact motion monitoring system in response to a moving subject are received by at least one receiving unit and attached thereto real time and other data processing equipment.

* * * * *